(12) United States Patent
Hug (10) Patent No.: US 9,146,190 B2
(45) Date of Patent: Sep. 29, 2015

(54) INSPECTION APPARATUS WITH ALTERNATE SIDE ILLUMINATION (75) Inventor: Anthony Hug, London (GB)

(73) Assignee: Buhler Sortex Ltd., London (GB)

( * ) Notice: Subject to any disclaimer, the term of this patent is extended or adjusted under 35 U.S.C. 154(b) by 0 days.

(21) Appl. No.: 14/129,385

(22) PCT Filed: Jun. 28, 2012

(86) PCT No.: PCT/GB2012/051514
§ 371 (c)(1),
(2), (4) Date: Mar. 21, 2014

(87) PCT Pub. No.: WO2013/001304
PCT Pub. Date: Jan. 3, 2013

(65) Prior Publication Data
US 2014/0226163 A1 Aug. 14, 2014

(30) Foreign Application Priority Data
Jun. 28, 2011 (EP) ...................................... 1111024

(51) Int. Cl.
G01N 21/55 (2014.01)
G01N 21/31 (2006.01)
G01N 21/85 (2006.01)

(52) U.S. Cl.
CPC ............ *G01N 21/3151* (2013.01); *G01N 21/85* (2013.01)

(58) Field of Classification Search
CPC .............. A61F 7/034; G01J 3/42; G01N 1/44
USPC .................. 356/335–337, 222, 215, 445, 436; 209/576–588
See application file for complete search history.

(56) References Cited

U.S. PATENT DOCUMENTS

| 5,538,142 A | * | 7/1996 | Davis et al. | .................... 356/407 |
| 5,669,511 A | * | 9/1997 | Satake et al. | .................. 209/580 |

(Continued)

FOREIGN PATENT DOCUMENTS

| DE | 3443476 | 5/1986 |
| EP | 1 818 152 | 8/2007 |

(Continued)

OTHER PUBLICATIONS

PCT, Notification Concerning Transmittal of International Preliminary Report on Patentability, in Application No. PCT/GB2012/051514, dated Jan. 16, 2014. (7 pages).

(Continued)

*Primary Examiner* — Tarifur Chowdhury
*Assistant Examiner* — Iyabo S Alli
(74) *Attorney, Agent, or Firm* — McAndrews, Held & Malloy, Ltd.

(57) ABSTRACT

Apparatus for inspecting product pieces in a product stream comprising a system for creating a stream of product pieces for delivery in free flight at a viewing station, first light means for illuminating the viewing station from one side with light for reflection from product therein, second light means for illuminating the viewing station from the other side with light for reflection from product therein, a scanning system for receiving light from the first and second illuminating means reflected from product pieces in the viewing station and transmitted across the viewing station, and means for activating the first and second light means alternately in first and second scanning phases to successively illuminate a product stream at the viewing station.

20 Claims, 6 Drawing Sheets

(56) References Cited

U.S. PATENT DOCUMENTS

2006/0016735 A1   1/2006  Ito et al.
2008/0308471 A1  12/2008  Huber et al.

FOREIGN PATENT DOCUMENTS

GB    2475344    5/2011
WO    98/18574   5/1998

OTHER PUBLICATIONS

Search Report corresponding to GB Patent Application No. 1111024.4, dated Oct. 21, 2011.

International Search Report for International Patent Application No. PCT/GB2012/051514, mailed Sep. 13, 2012.

* cited by examiner

INSPECTION APPARATUS WITH ALTERNATE SIDE ILLUMINATION

RELATED APPLICATION

This application is a 371 National Phase filing of international Patent Application Serial No. PCT/GB2012/051514 filed Jun. 28, 2012, which claims priority benefit of GB Patent Application No. 1111024.4 filed Jun. 28, 2011. Both applications are incorporated herein by reference in their entirety.

The present invention relates to a sorting and inspection apparatus, and particularly to optical inspection techniques for use in sorting and inspection apparatus, for example for inspecting and then sorting bulk food stuffs such as grain, rice, nuts, pulses, fruit and vegetables. Examples of such apparatus are described in International Patent Publication No: WO98/018574, European Patent Publication No: EP 0838274, US Patent Specification No: U.S. Pat. No. 4,630,736 and GB Patent Publication No: GB 2471885, the entire disclosures of which are hereby incorporated by reference.

In apparatus of these types, a stream of products to be sorted is delivered, usually in free flight, through an imaging zone and a sorting zone. In the imaging zone, designated defects are looked for, and in the sorting zone, any products on which defects have been identified, and which products are thus to be rejected, are removed or separated from the stream of products. The removal is usually by way of one or more blasts of gas, such as air, from one or more ejectors disposed adjacent the stream of products.

In such machines, the required throughput is normally determined by the production rates elsewhere in the processing plant. Normally though, the required throughput is high and is typically measured in tonnes per hour, whereby for small products, the throughput is very rapid, with large numbers being sorted every second.

Food producers often use sorting and inspection apparatus, such as optical sorting machines, to sense defects in their foodstuffs, and thus to allow the removal of any defective, i.e. non-standard, products from the product stream. This in turn allows the sorted product to meet a client's agreed grade or quality standard, but yet while still maximising the total production yield from the unsorted product stream to the best extent possible, in a given timeframe. The quality standard usually specifies individual maximum levels of contamination for different types of defect. For example, when sorting rice, the defects might be insect-damaged "peck-grains", or chalky grains or yellow grains, with maximum levels for these contaminants being say less than 0.1% peck, less than 1% chalky and less than 0.2% yellow. Some customers also specify restrictions on the numbers of grey grains.

As used herein, the term "defect" or "defective" should be understood to include both blemishes on articles being sorted and whole articles/products which are unsatisfactory for that reason, or for another reason. It can also include foreign material or extraneous product.

Optical sorting machines identify defects in the product being sorted by using known techniques, such as by continuously analysing images of product (or parts of products) in the stream, taken at the imaging zone using sensors. Output signals from an image analyser can then be used to allow a control system to instruct the ejectors as appropriate, so as to eject the defects identified in the images, and thus also the products featuring those defects.

Usually the sensors are optimised to detect a particular type of defect. However, a sensor, or a line on a sensor, can be optimised for a specific sorting criteria, which sensor or line on a sensor may then also happen to usefully detect another type of defect, either because a product has more than one type of defect or because the sorting criteria are not wholly independent of each other. Optimisation may be by having each sensor or line of sensor look at a particular wavelength of light, or set of wavelengths of light, such as by providing the sensor or the line of pixels of the sensor with a specific filter. Alternatively or additionally, the light source may be tuned to provide at the viewing window of the sensor, or for a line thereof, an illumination of the product steam characterised by a desired wavelength or set of wavelengths of light, or with an illumination that omits certain undesired wavelengths, so as to suit the defect detection optimisation. This also can be achieved with filters, for filtering the emitted light prior to illuminating the product stream. Flashing lights can also allow alternating light colours.

With regard to that optimisation, there is no certainty that a given optimisation will offer exclusive detection for a specific form of defect. For example, an optimised detection criteria for rice, designed to detect peck-grains, may also identify some chalky and some yellow grains for removal. Furthermore, even though a particularly optimised detection criteria will typically identify the majority of one type of defect, it can also incorrectly classify some good products as being defective, since the optimisation is not necessarily optimised or appropriate as a means of detection for other forms of defect. For this reason, different criteria detections, using more than one optimisation, can be carried out either simultaneously using prisms, or in series as the product passes down or across through the imaging zone, again potentially using a flashing light source with sequential variable colours, or using different filters on two or more sensors or two or more lines of a sensor). For example, a first defect criteria detection may be carried out in a first part or line of the imaging zone, potentially using a first flash of illumination, perhaps of a first colour, e.g. blue, and a second defect criteria detection may be carried out in a fractionally spaced, usually lower, second part or line of the imaging zone, potentially using a second flash of illumination, perhaps of a different colour, e.g. red. These serial detections then allow both for two optimised detections to be carried out so as to allow the sensor(s) to optimally check for two or more different defects, and thus offer detection by means of individual optimisations. Where appropriate or possible given the optimisations used and the given characteristics of the detected product, it could also allow for cross-checking or correlation between the sequential or separate detections made by the detection circuit.

A problem occurs, however, with sequential detections, whether using flashing illuminations or frame by frame detections, in terms of matching up one detection with the next, so as to allow a cross-check or correlation to be performed, and that is related to the fact that whereas the frequency of the flashing, or the frequency of the image frame rate, or both, is typically fixed for a given viewing zone of a sorting apparatus, the speed of passage (velocity) of the individual, sequential, products in the product stream passing through that viewing zone is not fixed at the imaging zone—some products are travelling faster than others. After all, a product's velocity can depend on a number of situational characteristics, such as the design/features of the apparatus, the characteristics of the products themselves, the ambient environmental conditions, and the individual interactions between the various elements and products involved. For example, in rice sorting equipment, where the rice grain is passing through the viewing zone effectively in free fall, the velocities in the feed plane, i.e. through the imaging zone, are typically going to be anywhere between 3.5 m/s and 4.3 m/s. As a result, the specific timing of the commencement of the passage of a particular product into each part of the viewing zone is somewhat random. As such, there can be variations in the detection images used for the two or more sequential steps in the detection process, from one line or one sensor to the next, thereby making it hard to cross-check the separate detections, and this can lead to variable detection accuracy. Attempts in the past to compensate for this have included trying to synchronise timing of flashed illumination to the products in the product stream, but that is too complicated, especially since a sorting apparatus may feature many separate product streams, each steam potentially being perhaps no more than a meter wide with a product flow in the order of more than one tonne per hour, and thus very densely populated with grains, and it is possible that the average speeds of those separate product streams will themselves be different or non-constant over time, since ambient condition can change or since different streams on a machine may have different functions, i.e. a flat or primary stream may have an average speed of 3.9 m/s and a re-sort or channelled stream may have an average speed of perhaps 3.5 m/s, and yet both may be on the same machine. Further, the multiple product streams are likely each to have their own viewing zone, and thus may have their own sensor(s) and light source(s). Therefore the product streams may be desired to be configured/synchronised separately for optimising detection performance.

The present invention is directed at apparatus of the above kind for inspecting product pieces in a product stream delivered in free flight to a viewing zone. The apparatus includes first and second light means for illuminating the viewing zone from opposite sides of the path along which the product pieces are delivered. A scanning system receives light from the first and second illuminating means reflected from product pieces in the viewing station and light transmitted across the viewing station. Signals generated by the scanning system are transmitted to a computer for analysis. Means are provided for activating the first and second light means alternately in first and second phases, to successively illuminate a product stream at the viewing station. This alternate illumination enables discolorations visible on both sides of a product piece to be identified, thereby enabling more comprehensive inspection to be accomplished.

In preferred embodiments of the invention, the apparatus can include auxiliary lighting behind the first and second light means on each side of the viewing station. This is additional to the first and second light means to provide background lighting respectively for the second and first light means in the respective phases. For example, in a first phase the first light means will illuminate the viewing station with light in the red and blue wavelength ranges, and the second light means will emit light only the red wavelength range. In the second phase, the second light means will be adapted to illuminate the viewing station with light in the red and blue wavelength ranges while the first light means will be adapted to emit light only in the red wavelength range. In this arrangement, it is preferred that the respective light means illuminate the viewing station from different angles. Background lighting can be provided in both phases, normally also in the red and blue wavelength ranges.

Instead of, or in addition to, the changes in wavelength (i.e. colour), it is possible for the changes or alternations to be in terms of the light's wave amplitude, i.e. its brightness or intensity. As such, the intensity of the illumination may be alternated or adjusted or changed to suit or optimise for the type of products being inspected, or to meet client requirements for product quality control, e.g. whiteness requirements for rice grains, or to correct for manufacturing tolerances in the light-source—e.g. the light output of the lamps or LEDs, which are not necessarily perfectly consistent from one light source to the next. Therefore, the first and second light means may emit light in different amplitude ranges. Further, or alternatively, the first and second light means may emit light in response to different or alternating electrical current inputs. Likewise, the auxiliary lighting may emit light in different, changing or alternating wavelength or amplitude ranges. Further, or alternatively, the auxiliary lighting may emit light in response to different, changing or alternating electrical current inputs.

The alternate activation of the first and second light means is very rapid, and as a consequence in each phase the same zone of the viewing station is illuminated from each side, with the scanning system receiving reflected light from the same product pieces. However, in order to accommodate the movement of product pieces between the first and second phases, the geometry of the pixels in the scanning system can be adjusted. This adjustment is described in more detail in our co-pending application filed today, entitled "Sorting and Inspection Apparatus with Camera Integration".

These and other features of the present invention will be apparent from the following description, given by way of example, and in which reference will be made to the accompanying drawings, in which:

FIGS. 7 and 8 relate to details of a possible camera data integration technique. They are discussed further in a co-pending application, concurrently filed by the present Applicant, entitled "Sorting and Inspection Apparatus with Camera Integration".

Figure 1:
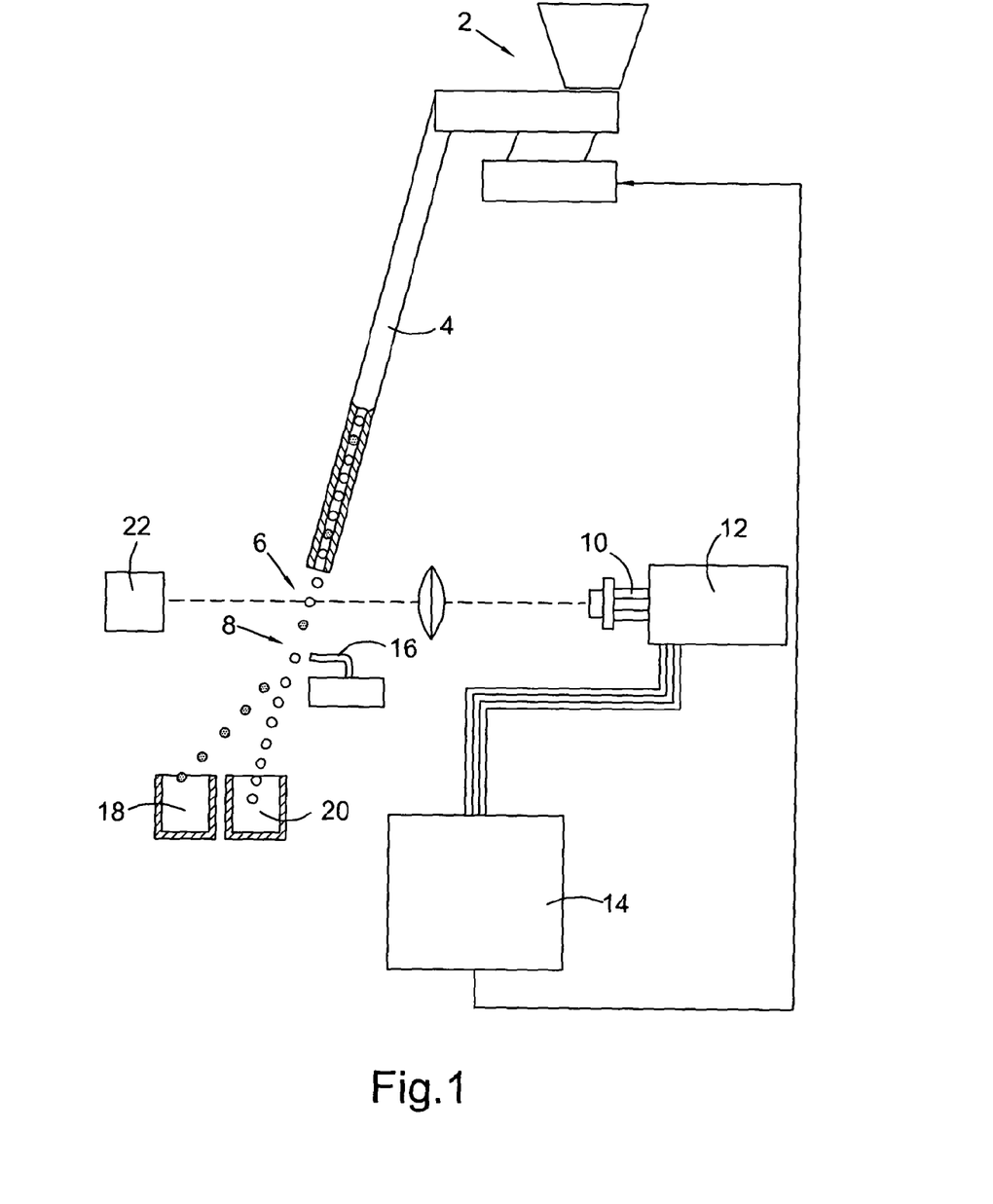
FIG. 1 is a schematic view of a sorting and inspecting apparatus according to the present invention.

Referring to FIG. 1, a sorting and inspection apparatus is illustrated. It has a hopper 2 in which the product to be sorted is loaded. It also has a product chute 4 down which the product to be sorted is fed—it is vibrated to the head of the chute by a vibrator-feeder mounted underneath the hopper 2.

The product chute is substantially vertical in this embodiment—perhaps at an angle of 15° from vertical. The chute may be flatter than this, however, if desired.

At the bottom of the chute—where the product exits the chute—a viewing zone 6 is provided. In this area, a sensor 10 and detection circuit 14 is provided for capturing images of the products as they fall through the viewing area at their individual product velocities and for making a determination as to whether the individual products have undesired defects. A projector 12 provided front-lighting for the products, whereas a backlight or background 22 can be used to assist with the prevention of erroneous defect detection, as known in the art.

Thereafter the products continue to fall—free fall—through a sorting zone 8, and in that sorting zone any product determined to have a defect is automatically ejected by an ejector 16, which is controlled by the detection circuit 14. Those defective products are therefore displaced by the ejector for collection in a defect bin 18. The good product, however, continues to fall into a good product bin 20.

The sensor 10 and detection circuit may also determine the velocity of the individual products, or a separate velocity sensor may be provided at the exit of the chute 4.

Illumination for the product, as it passes through the viewing zone may alternatively be provided by other, conventional, sorting/inspection machine lighting systems (not shown).

Figure 2:
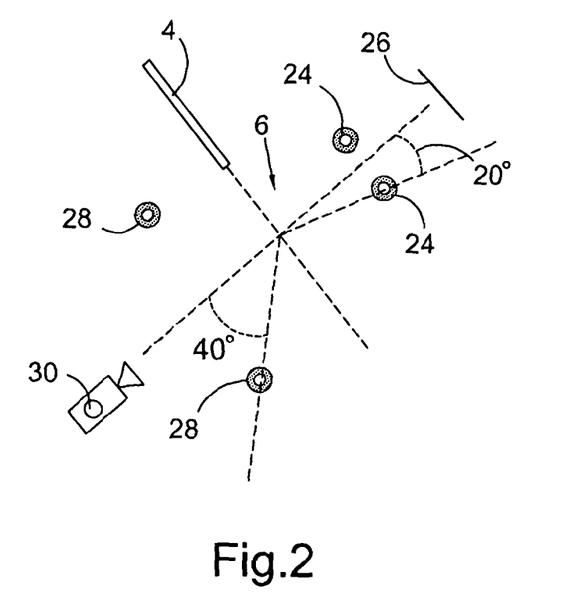
FIGS. 2 and 3 show a viewing zone for use in certain embodiments of the invention in which illumination of the products is phased to optimise the defect detection process.
Figure 3:
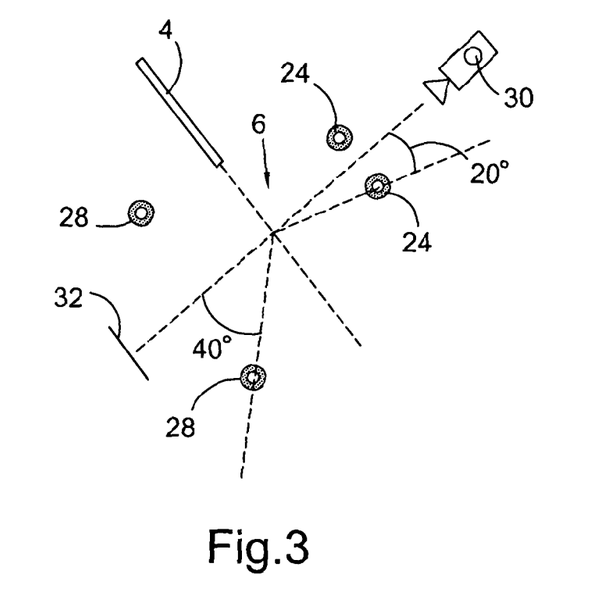

Referring next to FIGS. 2 and 3, further details of possible sensor/light source arrangements are provided.

The sorting apparatus described above can be referred to, in part, as a sorting module, i.e. a collection of items that makes up an identifiable part of a sorting machine and which may occur multiple times depending on machine capacity. Typically a sorting apparatus will consist of one chute plus associated vibrator(s), ejectors, and camera(s) with associated optics and processing. The sorting modules each may consist of one 300 mm wide chute, one vibrator (or two if split), 64 ejectors, four cameras each viewing 150 mm of product (front-left, front-right, rear-left and rear-right), four foreground and two background lighting blocks, and associated processing equipment. However, several of the functional elements might be shared between two or more sorting modules. This may lead to a modularity per machine or unit, for example as follows:

One frame.
Two views.
One HMI and system controller board (master unit only).
One system services board.
One vibrator controller board.
Three or more sorting modules.
at least one sorting board.

In the illustrated apparatus, for example when sorting rice, the product is expected to have a vertical velocity of between 3.57 ms-1 and 3.9 ms-1, and nominally 3.7 ms-1. However, feed plane velocities of between 3.5 ms-1 and 4.3 ms-1 are also likely to occur.

To provide a desirable sort performance with product speeds of this order, pixel dimensions at the feed plane should usually be no greater than 0.292 mm×0.292 mm. However, sorting processing costs can be proportional to the number of pixels used, so minimising the number of pixels has a cost saving benefit.

It is generally possible to achieve superior peck (small black spot) sorts with higher resolutions. Such defects are highly visible compared to shading changes/colour defects (yellows/greys/chalky grains) and are easily detectable using a single colour illumination.

Since peck requires simpler processing than colour defects, it is possible to process two separate defect detection data-streams from the sensors (which detect in two colours) independently, whereas for colour defects, bichromatic resolution data-stream is preferred.

It is also preferred to use a higher resolution monochromatic data-stream for spot defects than the resolution used for colour defects.

In view of this, the sensor arrangement may comprise a temporal delay based bichromatic system for determining colour defects, and additionally a higher resolution monochromatic sensor for detecting small black spots.

A preferred arrangement for rice grain sorting apparatus would include colour defect detection using a 0.292 mm×0.292 mm pixel resolution, bichromatically, and spot defect detection using a 0.146 mm X-axis (perpendicular to the flow)×0.292 mm Y-axis (parallel to the flow) pixel resolution, monochromatically.

The higher resolution enables smaller spots to be seen better—spot sizes on rice typically range between 0.875 mm square and 0.146 mm high (Y)×0.072 mm wide (X), and the pixel sizes listed above reflect an optimum arrangement for an electro-optic scan (EOS) period of 79.1 μs (i.e. where there is a target product velocity of 3.7 m/s). As such, in a preferred apparatus, 2048 pixels are capturing data over the product stream's full width (300 mm), with the image capture per pixel being 0.146 mm horizontally (X) and at 0.292 mm vertically (Y).

The sensor may have 512 lines, whereby an image of 2048 pixels by 512 lines can be captured from the camera for defect determination purposes.

To allow a synchronisation of various elements of the sensor, light source and defect determination parts of the apparatus a system sync signal is provided. It is preferred that the system sync signal be a square wave.

The signal's period is preferred to be modifiable within the range: 68 μs to 84 μs. This period is derived from the time required for a product (in this example a rice grain) to travel the distance between the two lines on the camera sensor. For the distance of 0.292 mm as given above, the above signal period range equates to product velocities of between about 4.3 ms-1 and about 3.5 ms-1.

A minimum signal period is preferably fixed so as to allow sufficient time to allow processing to take place.

In a preferred arrangement, the signal's period shall be modifiable in steps of no more than: 0.75 μs—this maximum step size is based on 1% of the nominal period.

The camera integration period shall be derived from the system sync signal.

It is necessary to be able to alter the camera integration period since the 'delay based' colour system (see below) needs to align the data for the two colours to the same (Y) position. This is done by assuming that the product has moved, during one scan period, from a first line of the sensor to the next, e.g. between a blue sensing line and a red sensing line, those lines collecting the relevant data during that scan period. The camera integration period is then altered to match the average, nominal or hypothetical velocity of the product in the product stream.

Referring next to FIGS. 2 and 3, the concept of phasing or phased illumination in the viewing zone will be discussed. It provides alternate illumination of opposite sides of the product stream and it helps to optimise the detection process.

In the arrangement shown, the front and rear views of the product have different lighting setups. Two camera/sensor/lighting/background arrangements are used, with the lighting arrangements being asymmetric.

As shown, product pieces are delivered in a stream from a chute 4 in free flight through a viewing zone indicated generally at 6. FIG. 2 shows a first phase in a scanning operation in which first light means in the form of arrays of light emitting diodes 24 illuminate product in the viewing zone 6. Light reflected from the product is received by the line scan camera 26 which generates and transmits signals to a computer (not shown) for analysis. As can be seen, the arrays of diodes 24 are disposed symmetrically on either side of the path of reflected light, at an angle of incidence of around 40°.

Lighting is provided in the first scanning phase shown in FIG. 2, by a second light means also in the form of arrays 28 of diodes on the other side of the viewing zone 6. The arrays 28 illuminate the viewing station from an angle different from that of the arrays 24, in the arrangement shown at an angle of incidence of around 20°. Background lighting is provided by an auxiliary light source 30.

In the arrangement shown in FIG. 2, in a first scanning phase, the LED arrays 24 illuminate the viewing station with light in the red and blue wavelength ranges while the LED arrays 28 provide lighting in the red wavelength range only. Background lighting (30) aligned with the camera 26 is also provided in the red and blue wavelength ranges.

In the second scanning phase illustrated in FIG. 3, the roles of the LED arrays 24 and 28 are reversed. The arrays 24 are switched to emit light only in the red wavelength range while the arrays 28 are switched to emit light in the red and blue wavelength ranges. In this phase, light reflected from product pieces in the viewing station is received by the camera 32 which generates and transmits signals to the computer for analysis.

Instead of, or in addition to, colour changes, the intensity of the illuminations may be changed or alternated.

While the LED arrays will continuously switch between scanning phases, the two cameras 26 and 32 can continue to receive reflected light and transmit signals to the computer during both phases. The computer can be programmed to discard data received but not required in a particular phase. Thus, the lighting alternates such that only in each phase does each camera have the lighting it requires. Illumination differences occur between the phases, however, due to the above indicated asymmetry.

With phasing, therefore, the front and rear views of the product should have different lighting setups—two camera/sensor/lighting/background arrangements are typically used. For example, the lighting arrangements shown in FIGS. 2 and 3 is asymmetric, with rear foregrounds at about 40° to the rear cameras and front foregrounds at about 20° to the front cameras.

These lighting setups may be mutually incompatible, but the concept of phasing serves to get around this issue.

Phasing can involve dividing the system sync period into two equal phases, 'phase #1' and 'phase #2'. Phase#1 might be used by the rear view camera, and it uses a same-side foreground red & blue lighting arrangement, with the other side foreground being red only lighting. Phase#2 might be used by the front view camera, also uses same-side foreground red & blue lighting, with the other side foreground being red only lighting. However, in this arrangement the lighting can be flashed such that only in each phase does each camera have the lighting it requires. Illumination differences occur between the phases, however, due to the above indicated asymmetry.

Any camera data captured during the phase meant for the other camera might be discarded—lights do not snap instantly on or off, so discarding such data can be helpful.

The flashing foreground lighting can be done with the two different configurations, as tied to the two phases of the system sync period.

The pixel geometry in the cameras is preferably modified such that in the product flow direction, the y-resolution of the detector photo-site equals the y-resolution of the machine (i.e. 0.292 mm in the example given).

Phase #1 might operate as follows (for rice sorting)—the rear view can separate out chalky, peck, dark yellows, subtle yellows, greys and paddy. The front view simply discards its data—it is too difficult to differentiate paddy from chalky from peck, or subtle yellows from greys. There are also problems with brown peck.

Phase #2 might operate as follows—rear view data is discarded, and for the front view, it is possible either to separate peck and paddy or to take a second shot at removing chalky, peck, dark yellows, subtle yellows, greys and paddy.

Other arrangements are possible within the scope of the invention.

Figure 4:
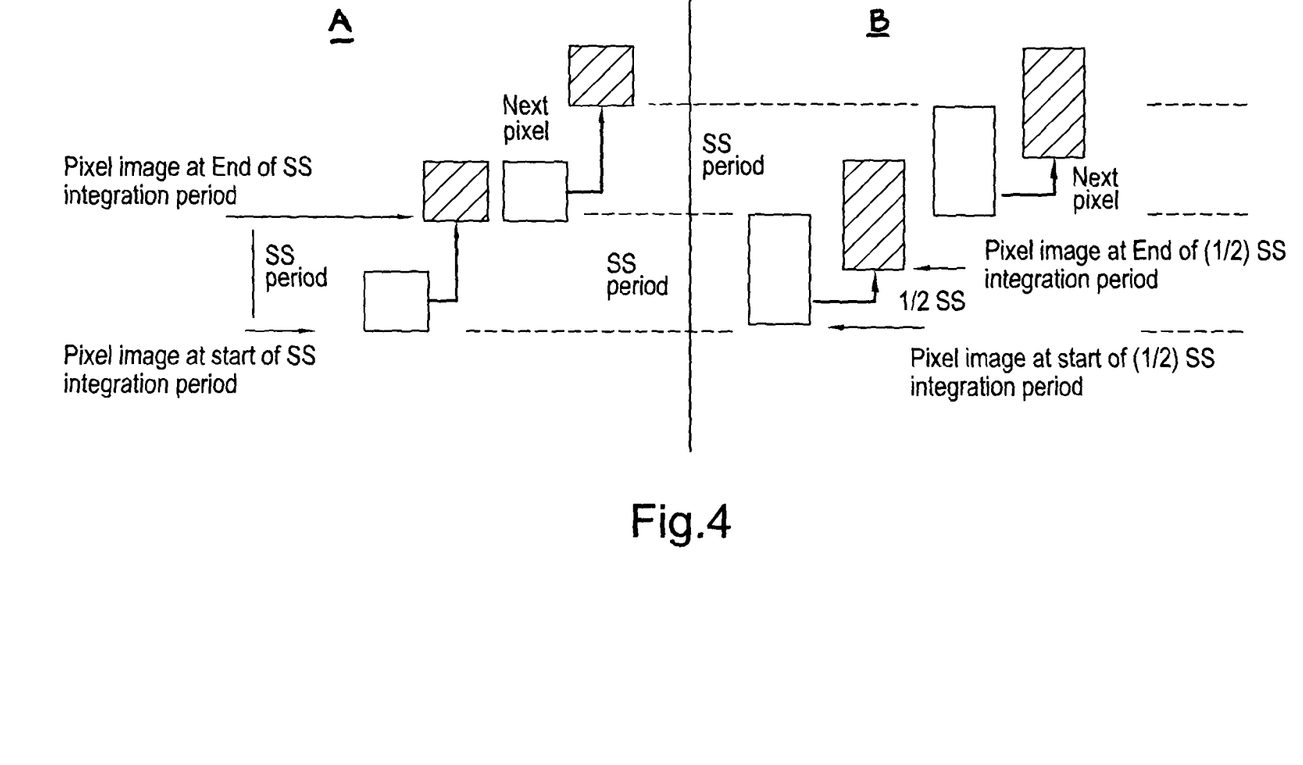
FIG. 4 illustrates the data collection improvement with the elongated pixels of the present invention compared to traditional square pixels.
Figure 5:
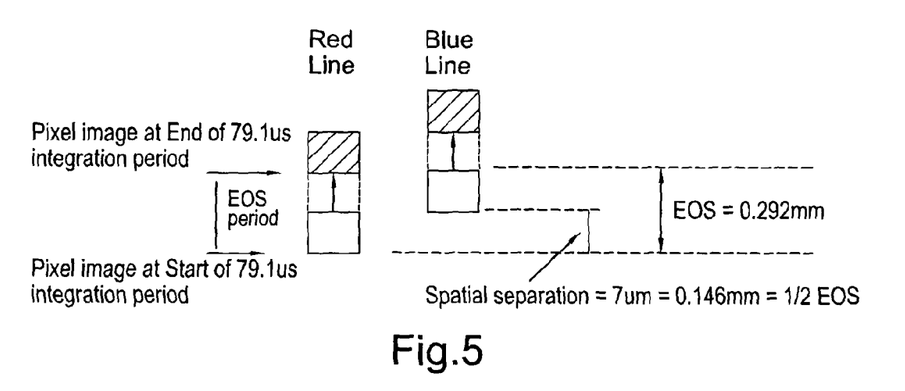
FIGS. 5 and 6 further illustrate the improvement in the quality of the collected data using elongated pixels (FIG. 6) compared to square pixels (FIG. 5)
Figure 6:
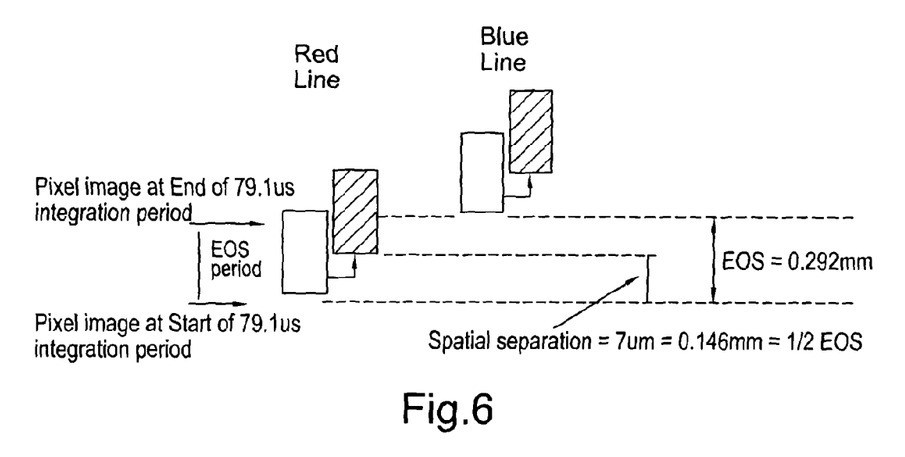

Referring next to FIG. 4, the following explains why a different geometry pixel is desired. FIG. 4 compares square pixels against the modified rectangular pixels (having a length of 0.292 mm). In the non-phasing square pixel case, a photo-site images ½ of the y-resolution of the system. At the start of an SS period, the photo-site images instantaneously, which in this case would be ½ y-resolution. Then, at the end of a full SS scan period, the pixel again images instantaneously a ½ y-resolution, with the distance the product has travelled in the SS period (set to be the y-resolution by system design) between these points. The pixel will integrate all the instantaneous values between these points.

In the Phasing case, the photo-site will image the full y-resolution initially instantaneously, such that after the ½ SS period, when integration of that photo-site stops, the end point will be at the same point as in the non-phasing case. The elongated pixel therefore captures the full amount of information, rather than just half of it.

The sorting apparatus also performs a defect detection using a spatiotemporally aligned sensor system, which is particularly useful for colour defect detection. This can be adopted using a sensor with two lines, one after the other, each with a discrete colour filter, where the colour alignment is achieved by temporally delaying one line output signal to match the other. This works well, and easily, where the product has fallen one line width distance between scans, i.e. it has a fixed velocity corresponding to the hypothetical velocity for which the system scan period is set. However, for products with a different velocity, such matching fails.

Nevertheless, to keep the data collection simple, the present invention's spatiotemporal alignment still involves setting the system scan period to the median of product chute (exit) velocity, and the collected data is processed to correct for velocity variations of even up to 20% from the median.

With the present invention, there is preferably only one scan period used by the apparatus—multiple scan periods can cause technical headaches in terms of synchronisation of the hardware, and the detection/ejection behaviour, plus pixel sizes and scan lengths would also vary across the apparatus. The present invention's single scan period therefore simplifies these elements, thus maintaining low manufacturing/set-up costs.

With the present invention, it is preferred that the foreground lighting is flashed, and this is done in synchrony with the scan period, and that too would make it impossible or difficult to support multiple scan periods, i.e. without having a machine of huge width (infill angle).

A difficulty with the single flash speed, however, is that it will not be optimised for the products travelling with the largest speed deviations from nominal. In particular there can be a trade off on exposure time (i.e. light).

The present invention therefore overcomes this by providing/creating a fixed width window (sector) that is smaller than the full window for that scan period within each ½ SS by using an exposure control. That sector or window may be slid anywhere within the ½ SS period as long as it is not clipped at either end. See FIG. 8.

Each 'colour' line of the sensor uses an independent window, and since each window can correspond fully to one from the other line, a good match is achievable for any velocity of product within the range of velocities expected. That is because the sectors are appropriately chosen to have the suitable temporal delay.

The change in temporal relationship between the exposure windows of the two sensor lines therefore translates into attempting to align the colours to product that has travelled different distances. The present invention therefore compensates for different product velocities.

Figure 7:
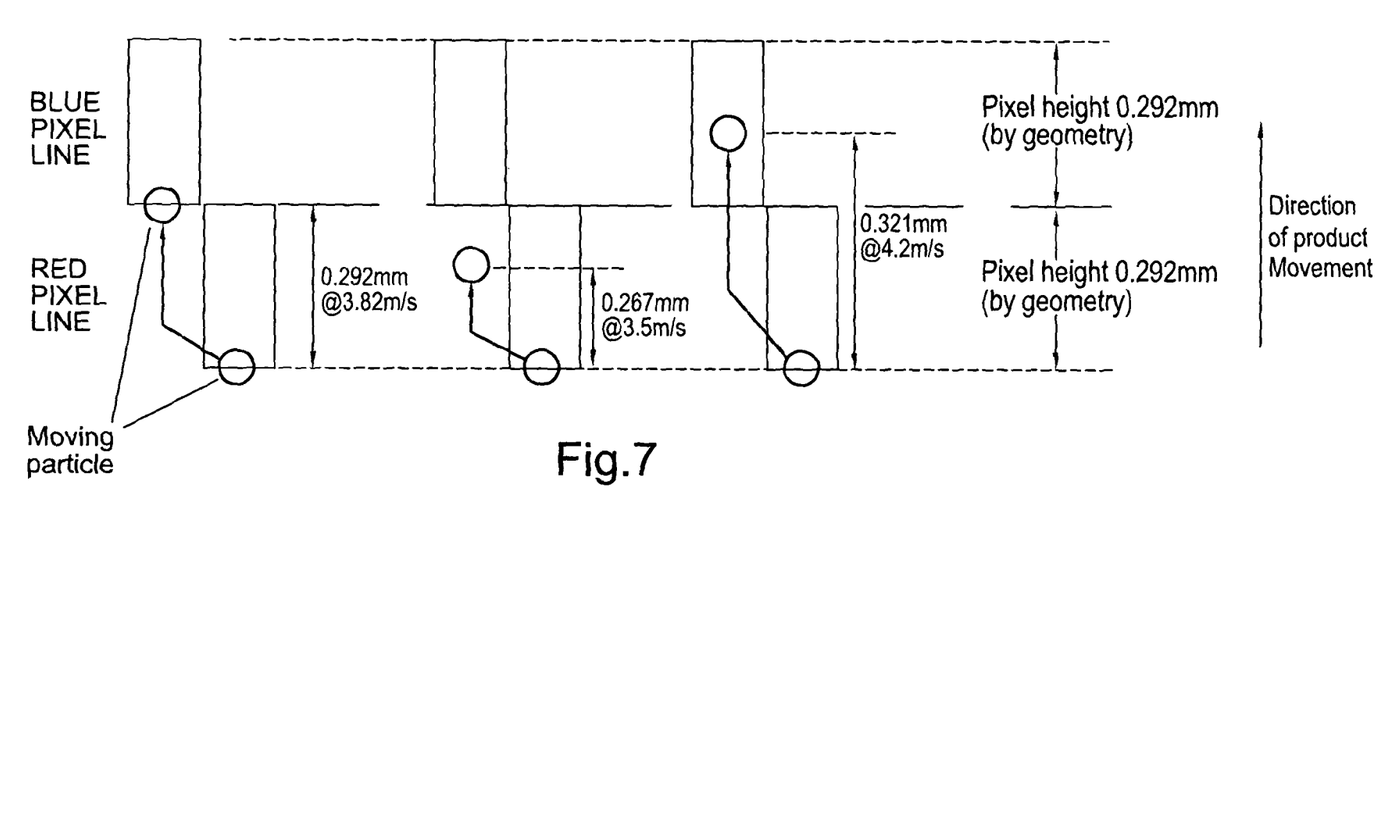
FIG. 7 shows the variance in travel distance across the sensing zone for products having different velocities.

FIG. 7 helps to illustrate the problem associated with products moving at different velocities through a viewing zone—it shows how far a particle moves with respect to the photosites of a 2 line sensor, one with a red filter, one with a blue filter, at different particle velocities.

Figure 8:
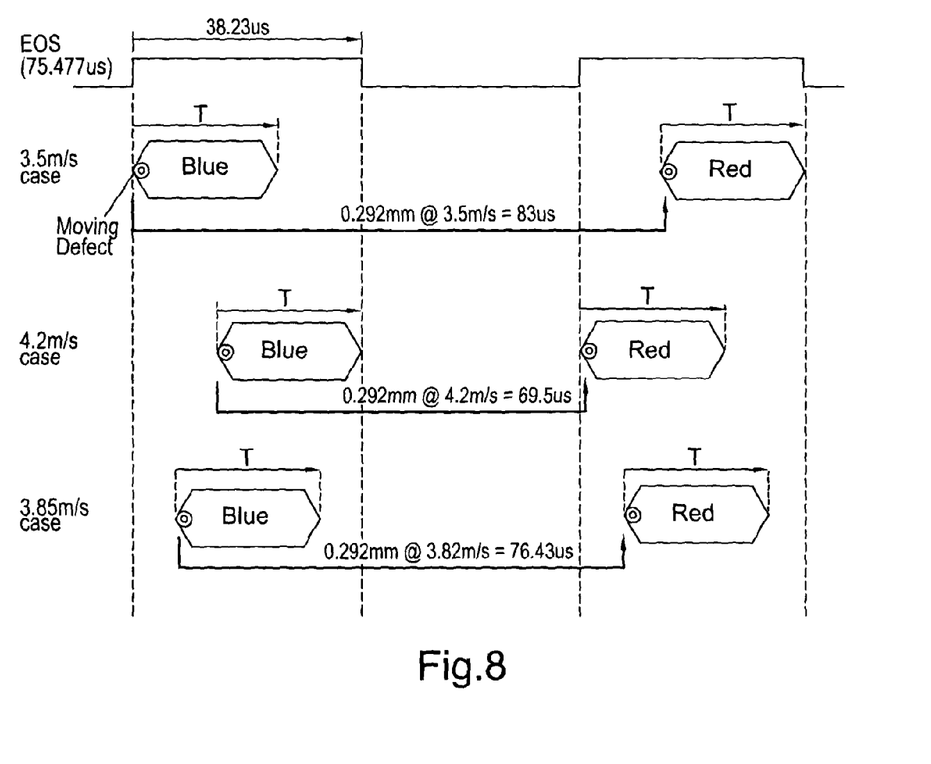
FIG. 8 illustrates the selection of sectors within the scan period for products having different velocities for optimising cross-checkability between defect determinations in separate lines of a sensor.

FIG. 8 then shows the solution using exposure control as exemplified by a moving defect for a case where the blue filtered sensor line is above the red filtered line.

Worst case average product velocities of 3.5 m/s and 4.2 m/s occurring on different chutes of the same machine are considered.

The System Sync (SS) has been set to the median delay equivalent to 0.292 mm at each of the extreme velocities.

$$\text{Median delay} = ((0.292 \text{ mm@}3.5 \text{ m/s}) + (0.292 \text{ mm@}4.2 \text{ m/s}))/2$$

$$= (83.429 \text{ us} + 69.524 \text{ us})/2$$

$$= 76.477 \text{ us}(3.82 \text{ m/s})$$

The solution requires that the sensor exposure of each of the colours be moved relative to each other in time within the lighting (½ SS) window provided.

Since we flash the LEDS, each ½ SS has the ideal lighting for either the front, or rear cameras.

In each case a defect or product point, just moving onto the active area of the blue sensor is considered, along with the time for that defect to move 0.292 mm, the area imaged by the pixel. For faster moving defects this time is shorter, for slower moving defects this time is longer.

The solution is considered optimal since with the exposure time of both the colours moving, each only has to move half the distance it otherwise would, and consequently the exposure window size can be kept as wide as possible (T=31.71 us).

The present invention has been described above purely by way of example. It will be appreciated, therefore, that modifications in detail may be made to the invention, as defined by the claims appended hereto.

Explanatory text for drawings:

| Figure | Text |
|---|---|
| 4 | A: Non-phasing square pixel case<br>B: Phasing rectangular pixel case |
| 5 | 1024 × 7 × 7 um pixels look over 150 mm (7 um = 0.146 mm) 2 colour lines next to each other |
| 6 | 1024 × 14 h × 7 w um pixels look over 150 mm (7 um = 0.146 mm) 2 colour lines next to each other |
| 7 | Shows movement of a particle of product after a time (dt) = time for 0.292 mm movement at 3.82 m/s<br>Blue/red pixels particles seen at same equivalent point (aligned) at 3.82 m/s obviously not at 3.5 m/s or 4.2 m/s |
| 8 | EOS @ 3.818 m/s (mean eos) = 76.477 us<br>Consider 3.5 m/s case: T = (3 × (½EOS)) − 83 us = 31.71 us<br>So Maximum Integration time = 31.71/38.23 × 100 = 83.0% maximum for ½EOS<br>To make up for this therefore we need 100 − 83 = 17% more Light (than we would otherwise at 76.43 us scan period)<br>100 − (31.71/39.59 × 100) = 20% more light than at the Z scan period (79.1 us) |

The invention claimed is:

1. Apparatus for inspecting product pieces in a product stream comprising:
    a system for creating a stream of product pieces for delivery in free flight at a viewing station;
    a first light comprising light emitting diodes for illuminating the viewing station from one side of the stream of product pieces with light for reflection from the product pieces; and
    a second light comprising light emitting diodes for illuminating the viewing station from the other side of the stream with light for reflection from the product pieces;
    wherein each of the first and second lights is operable to emit light in at least two different wavelength ranges and/or amplitude ranges in response to different electrical current inputs;
    the apparatus further comprising:
    a scanning system for receiving light from the first and second lights as reflected from the product pieces to each side of the stream in the viewing station and as transmitted across the viewing station; and
    a system for activating the first and second lights alternately in first and second scanning phases to successively illuminate the product pieces in the stream of product pieces at the viewing station whereby in the first scanning phase, the first light will emit light at a first wavelength or intensity, and the second light will emit light at a second wavelength range or intensity and in the second scanning phase, the first light will emit light at a wavelength or intensity different to the first wavelength or intensity, and the second light will emit light at a wavelength or intensity different to the second wavelength range or intensity.

2. Apparatus according to claim 1 wherein in the first scanning phase the first light emits light in the red and blue wavelength ranges and the second light emits light only in the red wavelength range.

3. Apparatus according to claim 1 including auxiliary lighting on each side of the viewing station to provide background lighting for each of the first and second lights.

4. Apparatus according to claim 3 wherein the respective lights illuminate the viewing station from the respective side at a first angle and the auxiliary lighting illuminates the respective opposite side from a second angle different from the first angle.

5. Apparatus according to claim 3, wherein the second light provides background lighting in the first phase and the first light provides transmissive lighting in the second phase.

6. Apparatus according to claim 1 including an auxiliary light behind each of the first and second lights for providing background illumination in the respective scanning phases.

7. Apparatus according to claim 6, wherein the auxiliary light emits light in different, changing or alternating wavelength or amplitude ranges.

8. Apparatus according to claim 6, wherein the auxiliary light emits light in response to different, changing or alternating electrical current inputs.

9. Apparatus according to claim 3, wherein the auxiliary lighting emits light in different, changing or alternating wavelength or amplitude ranges.

10. Apparatus according to claim 3, wherein the auxiliary lighting emits light in response to different, changing or alternating electrical current inputs.

11. Apparatus according to claim 1 wherein in the second scanning phase the second light emits light in the red and blue wavelength ranges and the first light emits light only in the red wavelength range.

12. Apparatus according to claim 1, wherein a system sync signal is provided to allow synchronization of various elements of the lights, the scanning system and the system for activating the first and second lights.

13. The apparatus according to claim 12, wherein the signal's period is within the range 68 μs and 84 μs.

14. Apparatus according to claim 3, wherein a system sync signal is provided to allow synchronization of various elements of the lights, the scanning system, the system for activating the first and second lights and the auxiliary lighting.

15. The apparatus according to claim 14, wherein the signal's period is within the range 68 μs and 84 μs.

16. The apparatus according to claim 6, wherein a system sync signal is provided to allow synchronization of various elements of the lights, the scanning system, the system for activating the first and second lights and the auxiliary lighting.

17. The apparatus according to claim 14, wherein the signal's period is within the range 68 μs and 84 μs.

18. A method of optical inspection, comprising
 a) providing an apparatus comprising:
  a system for creating a stream of product pieces for delivery in free flight at a viewing station;
  a first light comprising light emitting diodes for illuminating the viewing station from one side of the stream of product pieces with light for reflection from the product pieces;
  a second light comprising light emitting diodes for illuminating the viewing station from the other side of the stream with light for reflection from the product pieces;
  wherein each of the first and second lights is operable to emit light in at least two different wavelength ranges and/or amplitude ranges in response to different electrical current inputs;
  a scanning system for receiving light from the first and second lights as reflected from the product pieces to each side of the stream in the viewing station and as transmitted across the viewing station; and
  a system for activating the first and second lights alternately in first and second scanning phases to successively illuminate the product pieces in the stream of product pieces at the viewing station whereby in the first scanning phase, the first light will emit light at a first wavelength or intensity, and the second light will emit light at a second wavelength range or intensity and in the second scanning phase, the first light will emit light at a wavelength or intensity different to the first wavelength or intensity, and the second light will emit light at a wavelength or intensity different to the second wavelength range or intensity;
 b) delivering the stream of product pieces in free flight at the viewing station; and
 c) alternately activating the first light and the second light to illuminate the stream of product pieces through first and second scanning phases, wherein in the first scanning phase, the first light illuminates at a first wavelength or intensity, and the second light illuminates at a second wavelength or intensity and in the second scanning phase, the first light illuminates at a wavelength or intensity different to the first wavelength or intensity, and the second light illuminates at a wavelength or intensity different to the second wavelength or intensity.

19. A method according to claim 18, wherein a system sync signal is provided to allow synchronization of various elements of the lights, the scanning system and the system for activating the first and second lights.

20. The method according to claim 19, wherein the signal's period is within the range 68 μs and 84 μs.

* * * * *